(12) United States Patent
Mashin-Chi et al.

(10) Patent No.: US 10,588,787 B2
(45) Date of Patent: Mar. 17, 2020

(54) METHOD AND SYSTEM FOR VOLUME ESTIMATION OF BODILY OUTPUTS IN ABSORBENT ARTICLES

(71) Applicant: Fred Bergman Healthcare Pty Ltd., North Sydney (AU)

(72) Inventors: Hadi Mashin-Chi, North Bondi (AU); Mehdi Azimi, Lindfield (AU); Anushiya Arunachalam Kannan, Carlingford (AU)

(73) Assignee: Fred Bergman Healthcare Pty Ltd., North Sydney (AU)

( * ) Notice: Subject to any disclaimer, the term of this patent is extended or adjusted under 35 U.S.C. 154(b) by 579 days.

(21) Appl. No.: 15/194,892

(22) Filed: Jun. 28, 2016

(65) Prior Publication Data

US 2017/0000655 A1 Jan. 5, 2017

(30) Foreign Application Priority Data

Jun. 30, 2015 (AU) ................................. 2015902553

(51) Int. Cl.
*G01V 1/40* (2006.01)
*A61F 13/42* (2006.01)
(52) U.S. Cl.
CPC ........ *A61F 13/42* (2013.01); *A61F 2013/424* (2013.01)

(58) Field of Classification Search
None
See application file for complete search history.

(56) References Cited

U.S. PATENT DOCUMENTS

| 2014/0336606 | A1* | 11/2014 | Bewick-Sonntag | ......................... A61F 13/535 604/369 |
| 2016/0361209 | A1* | 12/2016 | Mashin-Chi | ............ A61F 13/42 |
| 2018/0333306 | A1* | 11/2018 | Ahong | ................. A61B 5/6843 |

* cited by examiner

*Primary Examiner* — Aditya S Bhat
(74) *Attorney, Agent, or Firm* — Zeller IP Group, PLLC; Serge Krimnus

(57) ABSTRACT

A method and an incontinence monitoring system for estimating a volume or a volume range of a bodily output in a combination absorbent article and wetness sensor. The system comprises a combination of an absorbent article and a wetness sensor, and a processor adapted to receive an input representative of an electrical variable of the wetness sensor indicative of the occurrence of a bodily output in the absorbent article and to process the input including: characterising the input to generate a vector that is representative of the bodily output, applying one or more functions to the vector to generate one or more possible volumes of the bodily output, generating a distribution of the possible volumes, and determining a volume or a volume range for the bodily output based on the distribution of the possible volumes.

20 Claims, 3 Drawing Sheets

METHOD AND SYSTEM FOR VOLUME ESTIMATION OF BODILY OUTPUTS IN ABSORBENT ARTICLES

CROSS-REFERENCE TO RELATED APPLICATIONS

This application claims foreign priority from Australian Patent Application No. 2015902553, filed on Jun. 30, 2015.

FIELD OF THE INVENTION

The present invention relates to the field of incontinence monitoring. The invention particularly, although not exclusively, relates to methods and systems for estimating a volume of a bodily output in an absorbent article, such as an absorbent pad, diapers, wound dressing or the like, containing one or more wetness sensors.

BACKGROUND OF THE INVENTION

Incontinence is a condition characterised by the uncontrolled release of bodily discharges from the bladder and/or bowel. Urinary incontinence refers to loss of bladder control resulting in involuntary or uncontrolled urination. Urinary incontinence is a condition that is particularly prevalent among infants as well as in the elderly and infirm and, at least in relation to adult sufferers, is more prevalent among women.

Incontinence is managed in care institutions such as hospitals, nursing homes, aged care facilities and the like by the use of absorbent articles, such as pads, diapers and the like that are worn by subjects. Periodic and manual checking is required to determine whether it is the correct time to change an absorbent article worn by a subject.

Incontinence indicators and detection systems including sensors contained in absorbent articles exist. Such systems can include sensors that are adapted for electrical connection to an electronic device, such as a transceiver, which sends a signal to a processing device when an incontinence event is occurring or has occurred in the absorbent article. The system is configured to measure an electrical variable, such as resistance, of a wetness sensor in the absorbent article and to determine whether an incontinence event has occurred and other characteristics of incontinence events which are occurring or have occurred. Such systems may be adapted to alert a carer to the occurrence of an incontinence event so that the carer may check the article and, if necessary, change the article.

Existing absorbent articles with incontinence sensors can only detect the occurrence of one wetness event in an absorbent article and cannot fully and efficiently utilize the available capacity of an absorbent article. For example, in existing arrangements absorbent articles may be changed upon the detection of a wetness event of, say, 200 mL which is a waste of resources if the absorbent article is designed to hold up to 600 mL of liquid.

Existing procedures for checking the wetness status of an absorbent article, that is the extent to which the capacity of the absorbent article has been reached, requires manually checking a wetness indicator which is normally located on the outer side of the absorbent article backsheet. A manual check is intrusive to the wearer, labour intensive, not a very accurate in representing the volume of liquid in the absorbent article, sensitive to the wearer's movement, pressure applied on the absorbent article, orientation of the wearer and the like, and not in real-time which may lead to a wearer having a soaked absorbent article on up until being manually checked.

The present invention aims to improve on methods and systems for incontinence monitoring.

The above discussion of background art is included to explain the context of the present invention. It is not to be taken as an admission that any of the documents or other material referred to was published, known or part of the common general knowledge in the patent area at the priority date of any one of the claims of this specification.

SUMMARY OF THE INVENTION

The present invention provides a method for determining a volume or a volume range of a bodily output in a combination absorbent article and wetness sensor, the method comprising:
  receiving an input representative of an electrical variable of a wetness sensor indicative of the occurrence of a bodily output in the absorbent article; and
  processing the input including:
    characterising the input to generate a vector that is representative of the bodily output;
    applying one or more functions to the vector to generate one or more possible volumes of the bodily output;
    generating a distribution of the possible volumes; and
    determining a volume or a volume range for the bodily output based on the distribution of the possible volumes.

Preferably, the distribution includes a frequency of the occurrences of the possible volumes in each of a plurality of volume intervals. In preferred embodiments, the distribution includes a probability distribution of the possible volumes, preferably in form of a histogram.

The step of determining a volume or a volume range for the bodily output based on the distribution of the possible volumes can include selecting the volume interval with a highest frequency of the occurrences of the possible volumes.

In embodiments, the one or more functions applied to the vector includes multiplying the vector with a plurality of predetermined vectors.

Preferably, the results of the multiplication of the vector with the plurality of predetermined vectors are summed with each of a plurality of predetermined second vectors to generate the plurality of possible volumes.

In embodiments, the step of determining a volume or a volume range for the bodily output based on the distribution of the possible volumes includes applying a further function to the distribution of the possible volumes.

The further function can include adding the output of a constituent function to the possible volumes of each volume interval multiplied by a frequency of the possible volumes in the volume interval and dividing by a total number of the possible volumes. In this embodiment, the constituent function is a function that is a constituent or is a sub-function of the further function. In other words, the application of the constituent function to the possible volumes makes up, at least in part, the further function.

Preferably, the output of the constituent function includes any one or more of a midpoint of the volume interval or an average, mean, median and mode of the possible volumes of the volume interval.

In embodiments, the method further includes adjusting the volume or the volume range according to an adjustment ratio.

Preferably, the adjustment ratio is derived from comparing cumulative determined volumes of one or more bodily outputs in the absorbent article with cumulative actual volumes of the bodily outputs in the absorbent article.

In embodiments, the method includes determining whether the input representative of the electrical variable is representative of a bodily output occurring in the absorbent article.

Determining whether the input representative of the electrical variable is representative of a bodily output occurring in the absorbent article can include comparing one or more elements of the input representative of the electrical variable with a set of predetermined thresholds.

In embodiments, the method includes providing a notification of the volume or the volume range for the bodily output to a user.

The volume or the volume range can be used for any one or more of:
- choosing the absorbent article size and/or capacity;
- determining the correct time to toilet;
- determining the correct time to change the absorbent article; and
- determining the wetness state of an absorbent article.

In another aspect, the present invention provides a method for detecting the occurrence of a bodily output in an absorbent article based on a volume of a bodily output determined according to the method, and embodiments thereof, described above.

Preferably, detecting whether a bodily output has occurred in the absorbent article includes comparing the determined volume with a threshold.

Characterising the input can include extracting any one or more of the following information from the input representative of the electrical variable, including:
a. the length of time that the mean of the electrical variable has a slope smaller than a predetermined value;
b. the length of time that the mean of the electrical variable has a slope greater than a predetermined value;
c. the length of time that the mean of the electrical variable has a slope greater than a predetermined value and smaller than another predetermined value;
d. the length of time that the mean of the electrical variable has a slope smaller than a predetermined value;
e. the mean of the electrical variable having a slope smaller than a predetermined value;
f. the mean of the electrical variable having a slope greater than a predetermined value;
g. the mean of the electrical variable having a slope greater than a predetermined value and smaller than another predetermined value;
h. the mean of the electrical variable having a slope smaller than a predefined value;
i. similarity of the patterns of the electrical variable from a prior event and an end event of the front sensor section and the mean of the electrical variable of the sensor section;
j. similarity of the patterns of the electrical variable from the prior event and the end event of the mid-front sensor section and the mean of the electrical variable of the sensor section;
k. similarity of the patterns of the electrical variable from the prior event and the end event of the mid-back sensor section and the mean of the electrical variable of the sensor section;
l. similarity of the patterns of the electrical variable from the prior event and the end event of the back sensor section and the mean of the electrical variable of the sensor section;
m. similarity of the patterns of the electrical variable from the prior event and the end event of the full-length sensor section and the mean of the electrical variable of the sensor section; and
n. event count identification.

In another aspect, the present invention provides an incontinence monitoring system for estimating a volume of a bodily output in a combination absorbent article and wetness sensor, the system including:
- a combination of an absorbent article and a wetness sensor;
- a processor adapted to receive an input representative of an electrical variable of the wetness sensor indicative of the occurrence of a bodily output in the absorbent article and to process the input including:
  - characterising the input to generate a vector that is representative of the bodily output;
  - applying one or more functions to the vector to generate one or more possible volumes of the bodily output;
  - generating a distribution of the possible volumes; and
  - determining a volume or a volume range for the bodily output based on the distribution of the possible volumes.

In embodiments, the volume or the volume range for the bodily output in the absorbent article is transmitted to a device to notify a user of the determined volume or volume range for the bodily output.

The system can further include any one or more of a display device, a haptic device and an audio device adapted for notifying a user of the determined volume or volume range for the bodily output.

In embodiments, the system includes an electronic device connected to the wetness sensor adapted to measure the electrical variable of the wetness sensor.

BRIEF DESCRIPTION OF THE DRAWINGS

The invention will now be described in more detail with reference to the accompanying figures which are illustrative of embodiments and examples thereof, wherein.

It is to be understood that the particulars of the figures are not to be construed as limiting to the generality of the invention described above.

DETAILED DESCRIPTION

Figure 1:
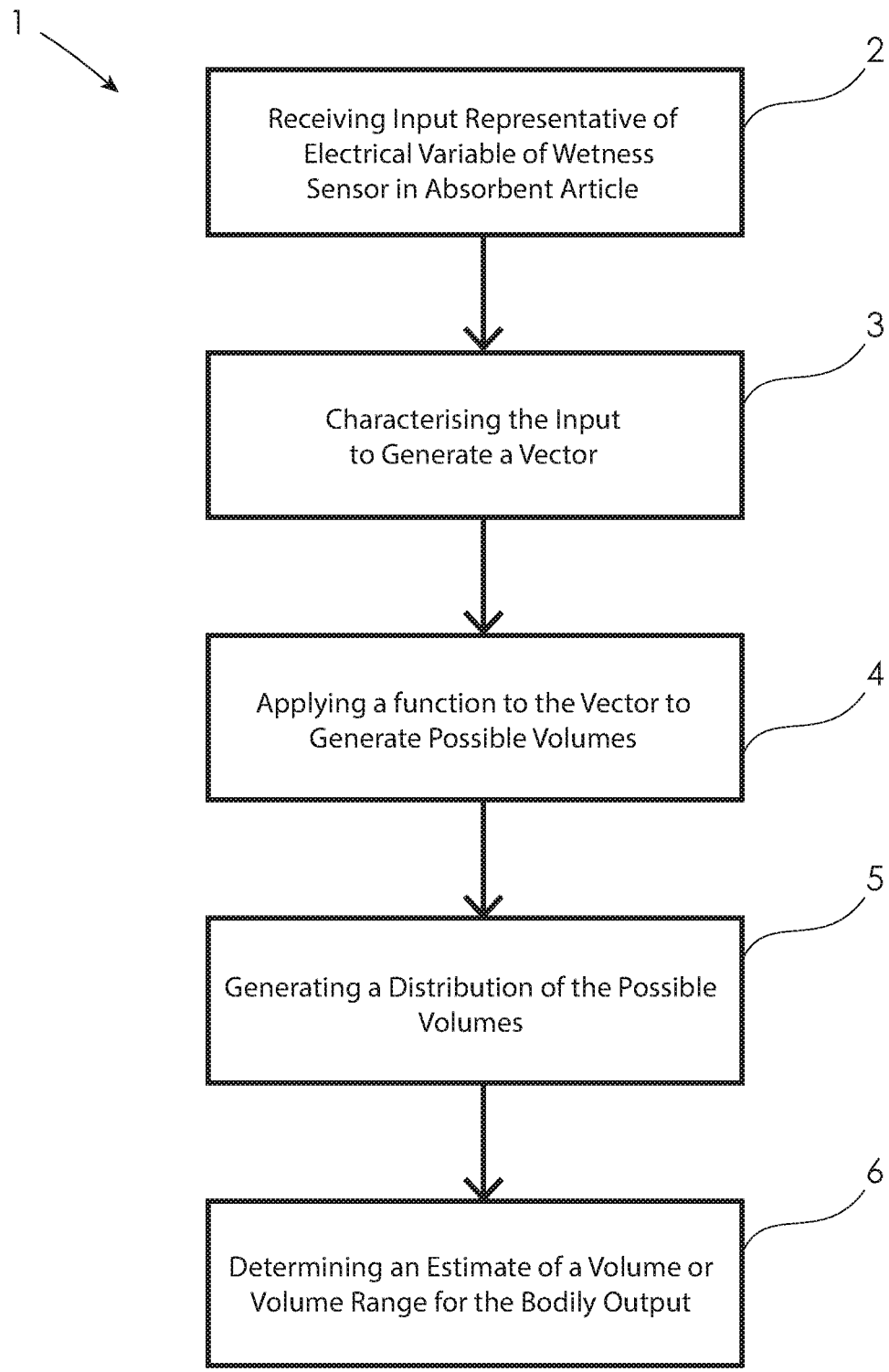
FIG. 1 illustrates a volume estimation method in accordance with an embodiment of the invention.

Referring to FIG. 1, there is shown an embodiment of the invention in the form of a volume estimation method at 1 for estimating a volume of a bodily output in an absorbent article. The method includes receiving an input representative of an electrical variable of a wetness sensor in a combination absorbent article and wetness sensor indicative of the occurrence of a bodily output in the absorbent article at 2. The input may be derived from a measurement of the electrical variable of the wetness sensor which may be taken continuously or when a bodily output occurs in the absorbent article. The method further includes processing the measured electrical variable to determine a bodily output volume which includes characterising the input to generate a vector that is representative of the bodily output at 3. The method further includes applying one or more functions, or in an embodiment applying a plurality of functions, to the vector to generate one or more possible volumes at 4. A distribution of the possible volumes is generated at 5 and a volume or a volume range for the bodily output is determined based on the distribution of the possible volumes at 6.

As will become apparent from the forgoing description, an embodiment of the step at 5 of generating a distribution of possible volumes includes generating a histogram with the plurality of possible volumes. The histogram includes volume intervals or bins plotted along an X axis and the possible volumes are allocated to the volume intervals or bins containing the respective volumes to produce a count or frequency of volumes in each volume interval or bin plotted along the Y axis. In an embodiment, the possible volumes are allocated in bins comprised of non-overlapping volume intervals or ranges and the bin containing the highest number or count of the possible volumes, in an embodiment, is used to determine the volume or a volume range for the bodily output.

Figure 2:
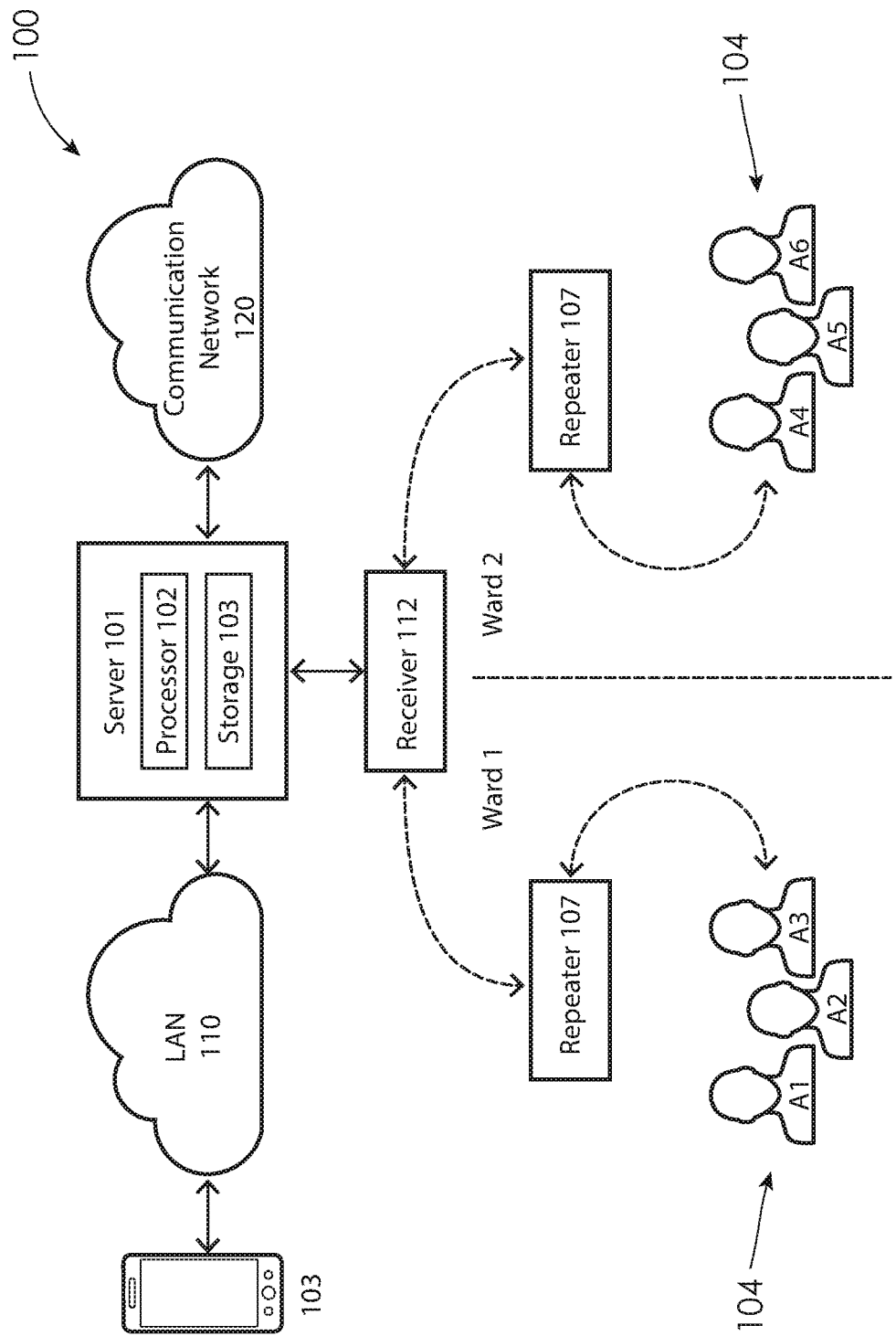
FIG. 2 illustrates an incontinence monitoring system for estimating a volume of a bodily output in an absorbent article containing a wetness sensor in accordance with an embodiment of the invention.

Referring to FIG. 2 there is shown an incontinence monitoring system 100 in accordance with an embodiment of the invention. The system 100 is employed in a care facility such as an aged care facility, hospital, child-care facility or other like facility. The system 100 is particularly adapted for monitoring incontinence in a number of subjects 104. The system 100 includes a server 101 comprising a processor 102 and a storage medium 103. The system 100 includes a receiver 112 that is adapted to receive signals from portable electronic devices A1-A6 associated with each of the subjects 104 being monitored by the system 100. The portable electronic devices A1-A6 are coupled to sensor devices within absorbent articles worn by each of the subjects 104.

Figure 3:
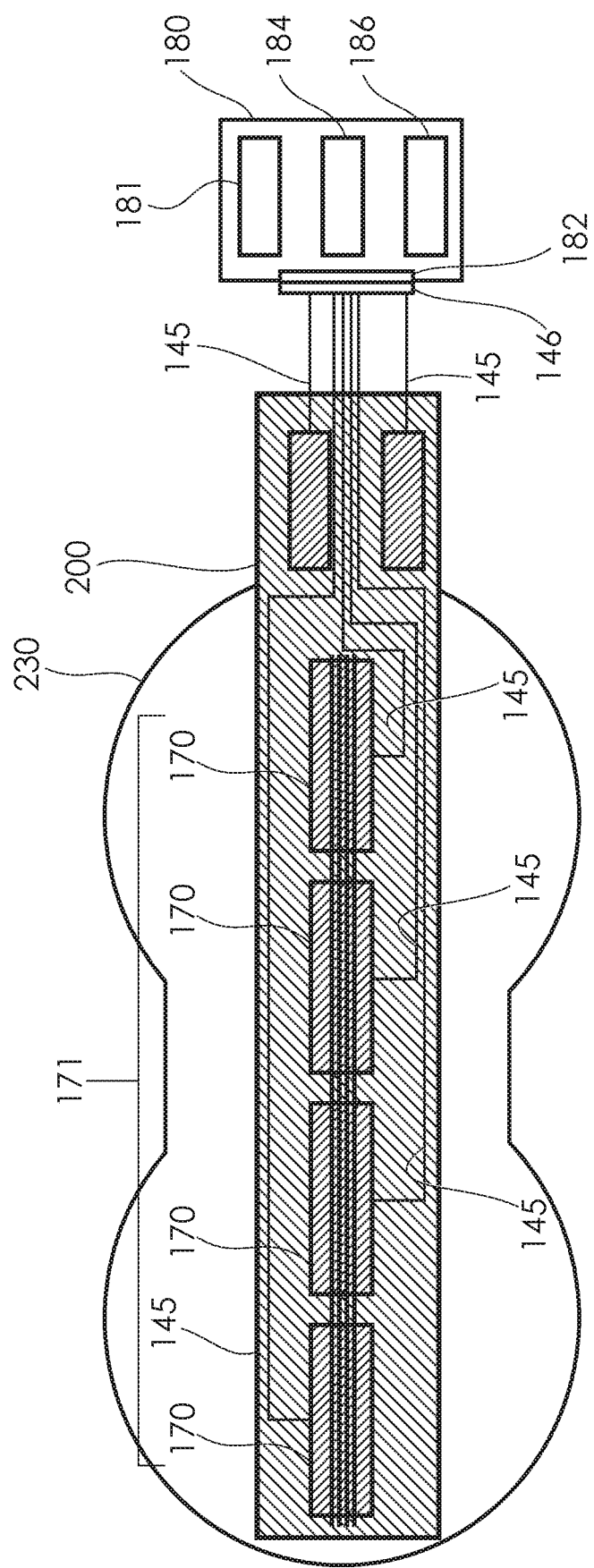
FIG. 3 illustrates an embodiment of the absorbent article and wetness sensor of the incontinence monitoring system of FIG. 2.

An embodiment of a sensor device 200 and absorbent article 230 is illustrated in FIG. 3 and is discussed in more detail below. For the purposes of describing embodiments of the present invention, the sensor device 200 may be described herein as being located in the absorbent article 230. It is to be appreciated, however, that embodiments of the combination absorbent article 230 and wetness sensor device 200 may include the sensor device 200 being, at least in part, located inside the absorbent article 230, outside the absorbent article 230 or comprising a sensor device 200 that is detachable from the absorbent article 230 and preferably being reusable.

The sensor device 200 is adapted to exhibit electrical behaviours that are affected by the occurrence of a bodily output in the absorbent article 230. The electrical behaviours can be characterised as electrical variables of the sensor device 200. For example, one or more electrical variables of the sensor device 200 can include resistance, voltage, current, capacitance and charge on a capacitor. Electrical variables of the sensor device 200 may be altered due to the presence of a bodily output in the absorbent article 230. As described below, the electrical variables of the sensor device 200 can be measured and information, a signal or an output representative of the electrical variable can be generated.

Referring to FIG. 3, the absorbent article 230 is of a form adapted to be worn by a subject suffering from incontinence. The absorbent article 230 includes the sensor device 200 provided therein during manufacture. The sensor device 200 includes one or more sensors 170, preferably including conductivity sensors, comprising one or more resistors although they may include permittivity sensors comprising one or more capacitors. The sensors 170 are electrically connected by conductors 145 to an electrical connector 146. The sensors 170 comprise a sensor array 171 contained within the absorbent article 230. The sensor array 171 illustrated in the embodiment of FIG. 3, is comprised of five resistivity sensors 170 comprising a front, mid front, mid back, back and full length resistivity sensor. The measured electrical variable, such as conductivity of the various sensors 170 following the occurrence of a bodily output in the absorbent article 230, is measured and processed in a manner described herein. In embodiments, the sensors 170 may be printed on the absorbent article 230, sensor device 200, or on adherable sensor sticker. The sensors 170 may be embedded differently in the absorbent article 230 for example on the coverstock of the absorbent article 230, under the overstock of the absorbent article 230, on the backsheet of the absorbent article 230, under the backsheet of the absorbent article 230, inside the absorbent article 230 or any other locations. The term "absorbent article" is to be taken as a reference to all absorbent articles including absorbent pads or garments wearable by subjects, diapers, inserts, incontinence pants, and the like. "Absorbent article" can further be a reference to wound care products including bandages and dressings.

Each of the portable electronic devices A1-A6 associated with each of the subjects 104 being monitored by the system 100 of FIG. 2 preferably includes an electronic device 180 as illustrated in FIG. 3. The electronic device 180 is adapted to be connected via an electrical connector 182 to the electrical connector 146 of the sensor device 200. The one or more sensors 170 are adapted to exhibit a change in electrical behaviour, such as resistance, permittivity or the like, with the presence of wetness (e.g. urine or other types of bodily outputs such as feces, blood, menstruation outputs, sweat and the like) in the absorbent article 230 resulting from the occurrence of a bodily output in the absorbent article 230. The presence of other matter such as enzymes or temperature may be measured by the sensor device 200. The change in electrical behaviour of the one or more sensors 170 is detected by measuring one or more electrical variables such as resistance, capacitance, voltage, current. The electronic device 180 coupled to the sensor device 200 is adapted to measure the one or more electrical variables of the sensor device 200 such as voltage, current, resistance, capacitance, charge on a capacitor or the like. The electronic device 180 includes a receiver 181, a processor 184 and a transmitter 186. Preferably, the processor 184 is adapted to either measure the one or more electrical variables or to cause the transmitter 186 to generate an output, such as in the form of a transmitted signal representing the one or more electrical variables to the repeater 107 or the receiver 112 of the system 100 illustrated in FIG. 2. In the latter case, the processor 102 in the server 101 receives an input representative of the one or more electrical variables of the sensor device 200 such as voltage, current, resistance, capacitance, charge on a capacitor or the like. In other embodiments, the processor 102 and the functions thereof may be in a portable or hand held device, in a cloud or in the electronic device 180 coupled to the sensor device 200.

Referring to the system 100 of FIG. 2, the output representative of the one or more measured electrical variables, such as a signal or some other form of information representative of the one or more electrical variables, is transmitted by the portable electronic devices A1-A6 to the receiver 112 directly or via a repeater 107 located, for example, in the ward containing the subject 104 which is then passed on to the receiver 112. The receiver 112 may be co-located with the server 101 or server 101 may be located remotely and may communicate wirelessly or via a wired connection or any other communications network with the receiver 112. The processor 102 is adapted to receive an input representative of the electrical variable and process the input, in accordance with embodiments of the present invention, to determine a bodily output volume or volume range (i.e. the volume of the bodily output or a volume range containing the volume of the bodily output).

The server 101 of the incontinence monitoring system 100 of FIG. 2 also is adapted to communicate by a local area network 110, such as a WIFI network and/or via a mobile telecommunications network, with one or more mobile electronic devices 103 operated by a carer, such as a nurse or the like, within the care facility. The mobile electronic device 103 may be a dedicated mobile electronic device or may be a smart-phone running an application configured for interoperability with the system 100 and the server 101 thereof via the local area network 110. The mobile electronic device 103 includes a display under the control of a processor and includes a visual representation of continence-related information obtained from monitoring bodily outputs occurring in the absorbent article worn by one of the subjects 104. A carer responsible for a subject being monitored uses the mobile electronic device 103 to receive alerts or to check the continence status of the subject 104 by viewing the visual representation. The mobile electronic device 103 may also convey visual, audible or other haptic reminders to carers to check the continence state of a subject or to perform an absorbent article change or assist the subject with a toileting event. The mobile electronic device 103 also includes an input that enables the carer to operate the device 103 and, in certain circumstances, input data into the system such as observations which may include absorbent article 230 size, capacity, type, manufacturer as well as the sensor device 200 type and, in particular, the weight of used absorbent articles 230 after changing. From the weight of used absorbent articles 230 after changing the cumulative volume of bodily outputs occurring in the absorbent article 230 can be determined which, as discussed in the forgoing description, is employed in further steps of embodiments of the method (i.e. to determine an adjustment ratio).

Embodiments of processing the input representative of the electrical variable to determine a bodily output volume, in accordance with the method of FIG. 1, will now be described. Processing the input preferably includes characterising the input to generate a vector, also referred to herein as an event vector, that is representative of the bodily output at 3. The step of characterising the input representative of the electrical variable preferably includes obtaining the signature of the electrical variable or data or a signal indicative of the electrical variable at any time including, in particular, during the occurrence of a bodily output in the absorbent article 230. Prior to obtaining the signature of the electrical variable, the method can include a step of smoothing the data or the signal indicative of the electrical variable. The smoothing step is carried out in order to remove noise that may exist in the data or signal due to factors such as the electrical components of the system, body movements of the subject wearing the absorbent article 230 and sensor device 200, pressure changes applied to the absorbent article and other extraneous factors.

Obtaining the signature of the electrical variable or of data or signal indicative of the electrical variable following the occurrence of a bodily output in the absorbent article 230 includes extracting any one or more of the following information a to n, hereinafter referred to as elements and intrinsic properties:

o. the length of time that the mean of the electrical variable has a slope smaller than a predetermined value;
p. the length of time that the mean of the electrical variable has a slope greater than a predetermined value;
q. the length of time that the mean of the electrical variable has a slope greater than a predetermined value and smaller than another predetermined value;
r. the length of time that the mean of the electrical variable has a slope smaller than a predetermined value;
s. the mean of the electrical variable having a slope smaller than a predetermined value;
t. the mean of the electrical variable having a slope greater than a predetermined value;
u. the mean of the electrical variable having a slope greater than a predetermined value and smaller than another predetermined value;
v. the mean of the electrical variable having a slope smaller than a predefined value;
w. similarity of the patterns of the electrical variable from a prior event and an end event of the front sensor section and the mean of the electrical variable of the sensor section;
x. similarity of the patterns of the electrical variable from the prior event and the end event of the mid-front sensor section and the mean of the electrical variable of the sensor section;
y. similarity of the patterns of the electrical variable from the prior event and the end event of the mid-back sensor section and the mean of the electrical variable of the sensor section;
z. similarity of the patterns of the electrical variable from the prior event and the end event of the back sensor section and the mean of the electrical variable of the sensor section;
aa. similarity of the patterns of the electrical variable from the prior event and the end event of the full-length sensor section and the mean of the electrical variable of the sensor section;
bb. event count identification—that is how many events have occurred before the current event.

The abovementioned means can be weighted means. Alternatively, instead of the mean of the electrical variable of a particular sensor being used a mean of the electrical variable of two or more sensors may be used, thus for example allowing for comparing the slope of, say the front sensor to a threshold, or comparing the slope of the mean of the front and mid-front sensors to a threshold. In another embodiment the similarity of the electrical variable of one sensor to one or more other sensors may be used as a signature. In yet another embodiment the similarity between the averages of electrical variables of multiple sensors data may be used as a signature. In yet another embodiment the similarity between parts identified in a, b, c, d of a plurality of sensors may be used as a signature.

It is to be appreciated that the signature of the electrical variable is not limited to the above and can include any measure that can extracted from the input representative of the electrical variable such as the area under a curve, slope of a curve, and the like.

After extracting the abovementioned properties, the processing step includes generating a vector of m intrinsic properties ip (where ip∈ℝ) comprising is represented by a $\vec{IP}$ as follows:

$$\vec{IP} = <ip_1, ip_2, ip_3, \ldots, ip_m>$$

Additional information such as the age, gender and weight of the person wearing the absorbent article 230 is added to the signature. Hereinafter, this additional information are referred to as extrinsic properties. The processing step includes generating a vector of n extrinsic properties ep (where ep∈ℝ) is represented by a $\vec{EP}$ as follows:

$$\vec{EP} = <ep_1, ep_2, ep_3, \ldots, ep_n>$$

Other extrinsic properties may include age, gender, and weight and may include environment temperature, environment humidity, type of the absorbent article, mobility of the person, and the like.

A vector which includes both intrinsic properties and extrinsic properties is generated that is referred to herein as the vector or the event vector. The event vector of size o with properties ev (where ev∈ℝ) is represented by a vector $\vec{EV}$ as follows:

$$\vec{EV} = <ev_1, ev_2, ev_3, \ldots, ev_o>$$

The event vector may comprise of all the intrinsic properties and the extrinsic properties. In another embodiment, a subset of properties are used in the event vector. In yet another embodiment, some or all of the elements in the event vector are a nonlinear combination of one or more of the intrinsic and the extrinsic properties. For example an event vector may be of the form:

$$\vec{EV} = <(ep_1), (ep_2) \cdot (ep_3), (ep_4) \cdot (ip_1), (ip_2)>.$$

The method includes applying a plurality of functions to the vector, also referred to herein as the event vector, to generate a one or more and preferably a plurality of possible volumes. An embodiment of this step includes multiplying the event vector with a plurality of predefined or predetermined vectors, also referred to herein as impact vectors. The plurality of impact vectors is herein also referred to as a volume matrix. The impact vector with o elements iv (where iv∈ℝ) is represented by a vector $\vec{IV}$ as follows:

$$\vec{IV} = <iv_1, iv_2, iv_3, \ldots, iv_o>^1.$$

The volume matrix with p impact vectors is represented by a vector $\vec{VM}$ as follows:

$$\vec{VM} = \begin{bmatrix} \vec{IV}^1 \\ \vec{IV}^2 \\ \vdots \\ \vec{IV}^p \end{bmatrix}.$$

The impact vectors may be varied depending on factors such as the event count ID, absorbent article size, absorbent article capacity and the like.

The impact vectors comprise a plurality of functions in accordance with an embodiment of the method of the invention which are applied to the event vector to generate a volume vector ($\vec{VV}$) representative of a plurality of possible volumes. The volume vector ($\vec{VV}$) is derived by:

1) Multiplying the event vector with each of the impact vectors which is an element-wise multiplication of two vectors, also known as a Hadamard product. The element-wise multiplication is represented by "∘". As an example the multiplication result of $\vec{EV}$ to $\vec{VM}$ is as follows:

$$\vec{EV} \circ \vec{VM} = \begin{bmatrix} ev_1 * iv_1^1 ev_2 * iv_2^1 & \ldots & ev_o * iv_o^1 \\ ev_1 * iv_1^2 ev_2 * iv_2^2 & \ldots & ev_o * iv_o^2 \\ & \vdots & \\ ev_1 * iv_1^p ev_2 * iv_2^p & \ldots & ev_o * iv_o^p \end{bmatrix}.$$

2) Then summing the values in each row as follows to generate Volume Vector ($\vec{VV}$):

$$\vec{VV} = \begin{bmatrix} ev_1 * iv_1^1 + ev_2 * iv_2^1 + \ldots + ev_o * iv_o^1 \\ ev_1 * iv_1^2 + ev_2 * iv_2^2 + \ldots + ev_o * iv_o^2 \\ \vdots \\ ev_1 * iv_1^p + ev_2 * iv_2^p + \ldots + ev_o * iv_o^p \end{bmatrix}$$

Each row of the volume vector $\vec{VV}$ represents one of the plurality of possible volumes of the bodily output derived from the measured electrical variable relating to the occurrence of the bodily output in the absorbent article 230.

In another embodiment, an additional step of adding each row of the volume vector $\vec{VV}$ to a predefined column vector (hereinafter referred to as offset vector), may be performed to generate a new volume vector $\vec{VV}$. The offset vector may be varied depending on factors such as the event count ID, absorbent article sizes, absorbent article capacity and the like. The offset vector with p elements ov (where ov∈ℝ) is represented by a vector $\vec{OV}$ as follows:

$$\vec{OV} = \begin{bmatrix} ov_1 \\ ov_2 \\ \vdots \\ ov_p \end{bmatrix}.$$

In another embodiment, an additional step of applying a function with an upper-bound asymptote or a lower-bound asymptote or both (hereinafter referred to as a bounded function) is performed on each row of the volume vector $\vec{VV}$ to generate a new volume vector $\vec{VV}$. The bounded function may be may be varied depending on factors such as event count ID, absorbent article sizes, absorbent article capacity and the like. For example if the bounded function is of a sigmoid type with lower bound of 0 and upper bound 400, then any estimated volume will be confined between 0 mL to 400 mL.

The method further includes generating a distribution, preferably a histogram, of the possible volumes and determining a volume or a volume range for the bodily output based on the distribution of the possible volumes. The distribution of the possible volumes represented by the volume vector $\overrightarrow{VV}$ is generated using b intervals, ranges bins etc., each interval having a length or bin size. In an embodiment, all bin sizes are the same except the very first and the last bin. For example, if b=4 and the bin sizes are the same then the bins are follows: $(-\infty, 150)$, $[150,300)$, $[300,450)$, and $[450,+\infty)$. The values for the number of bins, b, and the size of the bins depends on the resolution of the volume estimate required.

The distribution of the possible volumes is generated including a frequency or count of the occurrences of the possible volumes in each of the plurality of volume intervals or bins. From the generated distribution of the possible volumes, the method includes determining a volume or a volume range for the bodily output based on the distribution of the possible volumes. In one embodiment, this can include selecting the volume interval or bin with the highest count or frequency. Determining the volume or volume range for the bodily output may include applying a function on the possible volumes of the bin or interval with the highest frequency. In addition, or in the alternative, the step of determining a volume or volume range for the bodily output based on the distribution of the possible volumes can include summing outputs of a function applied on the possible volumes and multiplying by a frequency of the possible volumes in the bin or interval and dividing by a total number of the possible volumes.

Accordingly, in some embodiments, an interval that contains more estimated volumes is selected as the estimated volume range of the event. The ratio of the number of the estimated volumes in a given bin to the total estimated volumes may be used in a function to determine a degree of confidence that the bin containing the most estimated volumes is the correct volume or volume range of the bodily output.

In an embodiment, the estimated volumes in a bin with the highest number of the estimated volumes are used to estimate the volume of the bodily output. The mean and/or median of the estimated volumes may be used as an estimate of the volume of the bodily output. Alternatively the centre of the bin may be used as an estimate of the volume of the bodily output.

The function that may be applied on the possible volumes of the interval include average or mean of the possible volumes of the bin or interval.

The predetermined vectors for determining the volume and the volume range are derived by trial and error or during a training phase. In a training phase, a set of electrical variables with their known bodily output volume are divided into one or more of the training sets. A curve fitting function is then applied on each of the training set. The parameters of each fitted function for each of the training set is stored in one or more of a vector. For example if the curve fitting function is a linear regression analysis then the parameters of the linear function are the coefficients and the intercept. The coefficients and the intercepts of derived from the each of the training sets are then stored collectively in a vector $\overrightarrow{IV}$ and vector $\overrightarrow{OV}$, respectively.

In embodiments, the invention also involves a step of adjusting the determined volume or the determined volume range according to an adjustment ratio. The adjustment ratio is derived from comparing cumulative determined volumes in the absorbent article with cumulative actual volumes in the absorbent article. Such cumulative actual volumes may be determined by weighing the absorbent articles 230 after changing. Cumulative actual volumes and/or absorbent article weights 230 can be entered into the mobile device 103 of the system 100.

If the cumulative actual volume or weight of one or more bodily outputs occurring in an absorbent article 230 is known, then an adjustment can be made to the estimated volumes the bodily outputs to match the actual volume or weight of the bodily outputs. At any given time the total cumulative estimated volumes of the bodily outputs should be equal to the total cumulative volume or weight of the bodily outputs occurring in the absorbent article 230 and if they are not then an adjustment ratio can be derived as follows:

$$\text{Adjustment Ratio} = \frac{\text{sum of the estimated volumes}}{\text{known total weight of the bodily outputs}}.$$

The adjustment ratio can then be multiplied to the estimated volumes of the bodily output determined by the method.

In embodiments in which the method estimates a volume range of a bodily output occurring in an absorbent article 230 rather than the estimated volume then the adjustment ratio is multiplied to the start points and the end points of the estimated volume ranges. Alternatively, the midpoint of the estimated volume range can be multiplied by the adjustment ratio and the bin that contains the result is chosen as the estimated volume range.

In embodiments of the invention, the volume or the volume range is used for any one or more of the following purposes, namely choosing the absorbent article size and/or capacity that is to be worn by the subject 104, determining the correct time to toilet the subject 104 and/or determining the correct time to change the absorbent article.

An alternative aspect of the invention or embodiments of the previously mentioned aspect of the invention include a bodily output event detection method and system. That is, a method and system adapted to detect the occurrence of a bodily output in an absorbent article from an input representative of an electrical variable of a wetness sensor in an absorbent article received by a processor. The method and system including processing the input including characterising the input including generating one or more elements of the electrical variable, or of the input, and comparing the one or more elements with one or more thresholds to determine whether the electrical variable, or the input, is indicative of the occurrence of a bodily output in the absorbent article.

The aforementioned method and system, and embodiments thereof, can allow for filtering inputs representative of electrical variable measurements that are not, for whatever reason, considered to be indicative of a bodily output in the absorbent article. In an embodiment, the step of characterising the measured electrical variable includes comparing the one or more elements of the input representative of the electrical variable (e.g. information a to n listed herein) with a set of predetermined thresholds to determine if the measured electrical variable is indicative of a bodily output in the absorbent article. For example, the elements of a measured electrical variable that in one sense may be considered to resemble an event vector are compared with a set of predetermined thresholds to determine if the supposed event vector is, in fact, representative of a bodily output occurring in the absorbent article. If the comparison of the one or more elements of the input representative of the electrical variable with the set of predetermined thresholds indicatives that the input representative of the electrical variable measurement is not indicative of an actual bodily output in the absorbent article then the electrical variable measurement is discarded or not subjected to subsequent steps in the method including generating an event vector, applying a function thereto to generate a plurality of possible volumes and generating a distribution thereof.

Embodiments of the present invention are advantageous in that they can enable determination of a volume or volume range of a bodily output in an absorbent article and based on a comparison with the known capacity of the absorbent article can indicate to a carer whether the absorbent article is full and it is the correct time to change or is only partly full and it is not yet the correct time to change.

In this regard, embodiments of the method and the system can provide information in the form of an update to a carer on the wetness status of an absorbent article, such as how much of the absorbent capacity of the absorbent article has been utilised, while it is worn by a subject and preferably immediately after the occurrence of a wetness event, or as soon as possible thereafter (e.g. when the input representative of the electrical variable becomes available).

Embodiments of the present invention are advantageous in that they enable manual checking of the wetness status of an absorbent article to be done away with which reduces intrusion on the wearer and reduces labour. Embodiments of the present invention can also be more accurate than manual checking procedures in representing the volume of liquid in the absorbent article and can take into account the wearer's movement, pressure applied on the absorbent article, orientation of the wearer and the like, and can be in real-time or near real-time which may reduce the extent to which a wearer may have to endure a soaked absorbent article before being changed.

In further embodiments, the method and system can include a set of volume thresholds for a given absorbent article. Each pair of consecutive thresholds represents a band (or in another words a band can be represented by a lower threshold and an upper threshold). To determine the wetness status of an absorbent article, one should define what band the accumulative volume of wetness events discharged into the absorbent article belongs to. Each band is related to the capacity of an absorbent article. For example, for a particular absorbent article with thresholds of 250 mL, and 400 mL, the bands and the capacity representations are as follows:

from 0 to 250 mL: the absorbent article can still be worn by the wearer. In this instance, the wetness status of the absorbent article is "still OK to wear";

from 250 mL to 400 mL: the absorbent article should be changed if it contains any volume from 250 mL to 400 mL. In this instance, the wetness status of the absorbent article is "the absorbent article should be changed"; AND from 400 mL and greater: the absorbent article which contains a volume greater than 400 mL should have been changed before, (i.e. the volume of bodily output contained in the absorbent article is beyond the capacity of this absorbent article. In this instance, the wetness status is "soaked".

The abovementioned thresholds are dependent on the size of the absorbent article, the material and the amount of material used in the absorbent article (e.g. how much super absorbent material is used in an absorbent article), and also the user preference (i.e. how much urine an absorbent article can contain until it needs to be changed is indeed subjective and is different from one person to another).

In embodiments, the volume estimated for a wetness event discharged into an absorbent article is summed with the cumulative estimated volumes of prior wetness events discharged into the same absorbent article. The accumulative volume is then compared with the predefined thresholds to define what band the accumulative volume belongs to. The band which represents the wetness status of the absorbent article is notified to a person such as a carer via the mobile device 103, such as with a text message, audible or haptic notification or any other type of notification medium. For example, if the thresholds are 100 mL, 200 mL, 300 mL and the first wetness event occurring in the absorbent article is determined to be 210 mL then the wetness status associated with the band of 200 mL to 300 mL is recognized and the wetness status may be notified to a carer. When a second wetness event with a determined volume of 120 mL is detected then the wetness status associated with the band of greater than 300 mL is recognized, i.e. the accumulative volume is 330 mL. The updated wetness status may be notified to a carer.

The invention claimed is:

1. A method for estimating a volume of a bodily output received in a combination absorbent article and wetness sensor worn by a subject, the method comprising:
   receiving an input representative of a measured electrical variable of a wetness sensor indicative of the occurrence of a bodily output in the absorbent article; and
   processing the input including:
      characterising the input by extracting data indicative of one or more properties of the electrical variable to generate a vector that is representative of the bodily output;
      applying one or more functions to the vector to generate one or more possible volumes of the bodily output;
      applying a distribution function by allocating the possible volumes into bins each representing different volumes, wherein the distribution includes one or more bins each adapted to contain a count of multiple occurrences of the possible volumes; and
      estimating a volume of the bodily output based on the distribution of the possible volumes in the bins.

2. The method of claim 1, wherein estimating a volume of the bodily output is based on the distribution of the possible volumes in the bins with the highest frequency of the occurrences of the possible volumes.

3. The method of claim 1, wherein the one or more functions applied to the vector includes multiplying the vector with a plurality of predetermined vectors.

4. The method of claim 3, wherein each of the results of the multiplication of the vector with the plurality of predetermined vectors are summed with each of a plurality of predetermined second vectors to generate the plurality of possible volumes.

5. The method of claim 1, wherein estimating a volume of the bodily output based on the distribution of the possible volumes includes applying a further function to the distribution of the possible volumes.

6. The method of claim 5, wherein the further function includes adding the output of a constituent function to the possible volumes of each volume interval multiplied by a frequency of the possible volumes in the volume interval and dividing by a total number of the possible volumes.

7. The method of claim 6, wherein the output of the constituent function includes any one or more of a midpoint of the volume interval or an average, mean, median and mode of the possible volumes of the volume interval.

8. The method of claim 1, further including adjusting the volume according to an adjustment ratio.

9. The method of claim 8, wherein the adjustment ratio is derived from comparing cumulative determined volumes of one or more bodily outputs in the absorbent article with cumulative actual volumes of the bodily outputs in the absorbent article.

10. The method of claim 1, including carrying out an event detection step for determining if the measured electrical variable comprising the input is representative of a bodily output event occurring in the absorbent article.

11. The method of claim 10, wherein the event detection step includes comparing one or more elements of the measured electrical variable with a set of predetermined thresholds.

12. The method of claim 1, including providing a notification of the volume of the bodily output to a user.

13. The method of claim 1, wherein the volume is used for any one or more of:
choosing the absorbent article size and/or capacity;
determining the correct time to toilet;
determining the correct time to change the absorbent article; and
determining the wetness state of an absorbent article.

14. A method for detecting the occurrence of a bodily output in an absorbent article based on a volume of a bodily output estimated according to claim 1.

15. The method of claim 14, wherein detecting whether a bodily output has occurred in the absorbent article includes comparing the estimated volume with a threshold.

16. The method of claim 1, wherein the properties of the electrical variable include any one or more of:
a. the length of time that the mean of the electrical variable has a slope smaller than a predetermined value;
b. the length of time that the mean of the electrical variable has a slope greater than a predetermined value;
c. the length of time that the mean of the electrical variable has a slope greater than a predetermined value and smaller than another predetermined value;
d. the length of time that the mean of the electrical variable has a slope smaller than a predetermined value;
e. the mean of the electrical variable having a slope smaller than a predetermined value;
f. the mean of the electrical variable having a slope greater than a predetermined value;
g. the mean of the electrical variable having a slope greater than a predetermined value and smaller than another predetermined value;
h. the mean of the electrical variable having a slope smaller than a predefined value;
i. similarity of the patterns of the electrical variable from a prior event and an end event of the front sensor section and the mean of the electrical variable of the sensor section;
j. similarity of the patterns of the electrical variable from the prior event and the end event of the mid-front sensor section and the mean of the electrical variable of the sensor section;
k. similarity of the patterns of the electrical variable from the prior event and the end event of the mid-back sensor section and the mean of the electrical variable of the sensor section;
l. similarity of the patterns of the electrical variable from the prior event and the end event of the back sensor section and the mean of the electrical variable of the sensor section;
m. similarity of the patterns of the electrical variable from the prior event and the end event of the full-length sensor section and the mean of the electrical variable of the sensor section; and
n. event count identification.

17. An incontinence monitoring system for estimating a volume of a bodily output received in a combination absorbent article and wetness sensor worn by a subject, the system including:
a combination of an absorbent article and a wetness sensor for wearing by a subject;
a processor adapted to receive an input representative of a measured electrical variable of the wetness sensor indicative of the occurrence of a bodily output in the absorbent article and to process the input including:
characterising the input by extracting data from the electrical variable to generate a vector that is representative of the bodily output, the vector being comprised of data indicative of a plurality of different properties of the electrical variable;
applying one or more functions to the vector to generate one or more possible volumes of the bodily output;
applying a distribution function by allocating the possible volumes into bins representing different volumes, wherein the distribution includes one or more bins each adapted to contain a count of multiple occurrences of the possible volumes; and
estimating a volume for the bodily output based on the distribution of the possible volumes in the bins.

18. The system of claim 17, wherein the volume for the bodily output is transmitted to a device to notify a user of the determined volume or volume range for the bodily output.

19. The system of claim 17, further including a display device, a haptic device or an audio device adapted for notifying a user of the determined volume or volume range for the bodily output.

20. The system of claim 17, including an electronic device connected to the wetness sensor adapted to measure the electrical variable of the wetness sensor.

* * * * *